United States Patent

Harada et al.

[11] Patent Number: 6,127,397
[45] Date of Patent: Oct. 3, 2000

[54] OPTICALLY ACTIVE (R)-(E)-(4-SUBSTITUTED-PHENYL-1,3-DITHIOLAN-2-YLIDENE)-1-IMIDAZOLYLACETONITRILE DERIVATIVE, ANTIFUNGAL COMPOSITION COMPRISING THE SAME, AND METHOD FOR PRODUCING THE SAME

[75] Inventors: Koichiro Harada, Osaka; Takashi Kagawa, Wakayama; Yuri Goto, Osaka; Masanori Yoshida, Wakayama, all of Japan

[73] Assignee: Nihon Nohyaku Co., Ltd., Tokyo, Japan

[21] Appl. No.: 08/986,168

[22] Filed: Dec. 5, 1997

[30]  Foreign Application Priority Data

Dec. 10, 1996  [JP]  Japan .................... 8-346692

[51] Int. Cl.[7] .................... A61K 31/4178; C07D 409/06
[52] U.S. Cl. .................... 514/397; 548/315.1
[58] Field of Search .................... 514/397; 548/315.1

[56]  References Cited

U.S. PATENT DOCUMENTS

| | | | |
|---|---|---|---|
| 4,636,519 | 1/1987 | Seo et al. | 514/397 |
| 4,738,976 | 4/1988 | Seo et al. | 514/341 |
| 5,900,488 | 5/1999 | Kodama | 548/315.1 |

FOREIGN PATENT DOCUMENTS

| | | | |
|---|---|---|---|
| 0218736 | 9/1985 | European Pat. Off. | |
| 2-275877 | 11/1990 | Japan . | |
| Wo 97/02821 | 1/1997 | WIPO | A61K 31/415 |

OTHER PUBLICATIONS

European Patent Office, Abstract of Japan (in English), No. 02275877, "Optically Active Ketene Dithiocetal Derivative And Its Production," publication date Nov. 9, 1990.

European Patent Office, Abstract of Japan (in English), No. 01242528, "Antifungal Agent For External Use," publication date Sep. 27, 1989.

European Patent Office, Abstract of Japan (in English), No. 62093227, "Antimycotic Agent," publication date Apr. 28, 1987.

European Patent Office, Abstract of Japan (in English), No. 62093204, "Non–Medical Fungicide And Production Thereof," publication date Apr. 28, 1987.

*Primary Examiner*—Michael G. Ambrose
*Attorney, Agent, or Firm*—Sughrue, Mion, Zinn, Macpeak & Seas, PLLC

[57]  ABSTRACT

An optically active (R)-(E)-(4-substituted-phenyl-1,3-dithiolan-2-ylidene)-1-imidazolylacetonitrile derivative represented by the following formula (I) or a salt thereof:

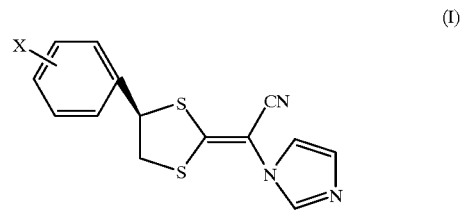

(I)

wherein X represents 1 to 5 substituents which are the same or different and are selected from the group consisting of a halogen atom, an alkyl group, a haloalkyl group and a haloalkoxy group, provided that X does not represent a 2-chloro group or a 2,4-dichloro group; an antifungal composition comprising the same; and a process for producing the same.

5 Claims, No Drawings

OPTICALLY ACTIVE (R)-(E)-(4-SUBSTITUTED-PHENYL-1,3-DITHIOLAN-2-YLIDENE)-1-IMIDAZOLYLACETONITRILE DERIVATIVE, ANTIFUNGAL COMPOSITION COMPRISING THE SAME, AND METHOD FOR PRODUCING THE SAME

FILED OF THE INVENTION

The present invention relates to an optically active antifungal agent having a more improved antifungal activity than the racemic mixture thereof in the field of medical antifungal compounds. The optically active composition according to the present invention is an antifungal agent useful for preventing or treating mycoses of human and animals. For example, the composition can be used for preventing or treating local mycotic infection, mucosa infection, or generalized mycotic infection caused by the genus of Trichophyton, Candida or Aspergillus.

BACKGROUND OF THE INVENTION

Conventionally, various azole compounds having an antifungal activity are known. For example, JP-A-60-218387 and JP-A-62-93227 (the term "JP-A" as used herein means an "unexamined published Japanese patent application") disclose that the imidazole derivatives are useful as an antifungal agent. Furthermore, JP-A-2-275877 discloses that specified optically active compounds among the above imidazole derivatives have an antifungal activity against *Trichophyton mentagrophytes* about 1.4 times the activity of racemates thereof.

SUMMARY OF THE INVENTION

An object of the present invention is to provide optically active compounds of imidazole derivatives having a more excellent antifungal activity than racemates thereof.

A further object of the present invention is to provide a process for producing the optically active compounds and a method for using them.

These and other objects of the present invention have been accomplished by an optically active (R)-(E)-(4-substituted-phenyl-1,3-dithiolan-2-ylidene)-1-imidazolylacetonitrile derivative represented by the following formula (I) or a salt thereof:

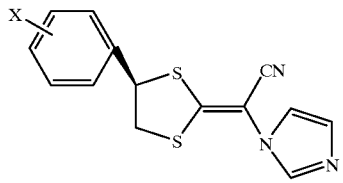

(I)

wherein represents 1 to 5 substituents which are the same or different and are selected from the group consisting of a halogen atom, an alkyl group, a haloalkyl group and a haloalkoxy group, provided that X does not represent a 2-chloro group or a 2,4-dichloro group.

Furthermore, these and other objects of the present invention have been accomplished by an antifungal composition comprising as an active ingredient the optically active (R)-(E)-(4-substituted-phenyl-1,3-dithiolan-2-ylidene)-1-imidazolylacetonitrile derivative as defined above or a pharmaceutically acceptable salt thereof, optionally together with a pharmaceutically acceptable carrier or diluent.

Moreover, these and other objects of the present invention have been accomplished by a process for producing the (R)-(E)-(4-substituted-phenyl-1,3-dithiolan-2-ylidene)-1-imidazolylacetonitrile as defined above or a salt thereof, comprising reacting an optically active glycol derivative represented by the following formula (II) or an equivalent thereof:

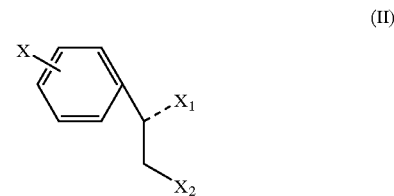

(II)

wherein X represents 1 to 5 substituents which are the same or different and are selected from the group consisting of a halogen atom, an alkyl group, a haloalkyl group and a haloalkoxy group; and $X_1$ and $X_2$ are the same or different and each represents a methanesulfonyloxy group, a benzenesulfonyloxy group, a p-toluenesulfonyloxy group or a halogen atom, provided that X does not represent a 2-chloro group or 2,4-dichloro group, with a dithiolate salt represented by the following formula (III):

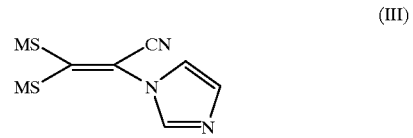

(III)

wherein M represents an alkali metal atom.

Also, these and other objects of the present invention have been accomplished by a method for preventing or treating local or generalized mycoses comprising administrating to human or animals in need of such prevention or treatment a pharmaceutically effective amount of the optically active (R)-(E)-(4-substituted-phenyl-1,3-dithiolan-2-ylidene)-1-imidazolylacetonitrile derivative as defined above or a pharmaceutically acceptable salt thereof, optionally together with a pharmaceutical acceptable carrier or a diluent.

Still furthermore, these and other objects of the present invention have been accomplished by use of the optically active (R)-(E)-(4-substituted-phenyl-1,3-dithiolan-2-ylidene)-1-imidazolylacetonitrile derivative as defined above or a pharmaceutically acceptable salt thereof for preparing an antifungal composition.

DETAILED DESCRIPTION OF THE INVENTION

In the present invention, optically active (R)-enantiomer compounds having an antifungal activity represented by formula (I) are selectively produced by an asymmetric synthesis. The compound thus produced and pharmaceutically acceptable salts thereof have an antifungal activity against fungi such as dermatophytes, *Trichophyton mentagrophytes* and *Trichophyton rubrum* several times the activity of the racemic mixture thereof.

In the definition of X in formula (I), the alkyl group represents a straight or branched $C_1$–$C_6$ alkyl group; the haloalkyl group represents a $C_1$–$C_6$ alkyl group substituted with one halogen atom or plural halogen atoms which are the same or different; and the haloalkoxy group represents a $C_1$–$C_6$ alkoxy group substituted with one halogen atom or plural halogen atoms which are the same or different. M in the formula (III) represents an alkali metal atom such as sodium and potassium.

Optically active compounds represented by formula (I) can be produced by the process shown in Reaction 1 according to the production method of a racemate described in JP-A-2-275877.

Reaction 1

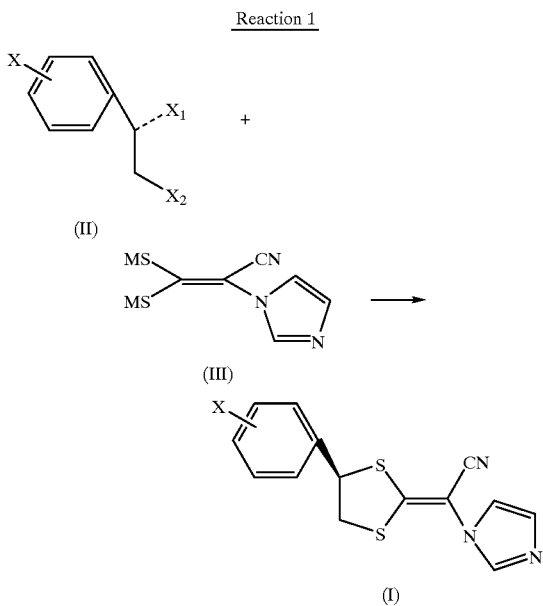

wherein X represents 1 to 5 substituents which are the same or different and are selected from the group consisting of a halogen atom, an alkyl group, a haloalkyl group and a haloalkoxy group; $X_1$ and $X_2$ are the same or different and each represents amethanesulfonyloxy group, a benzenesulfonyloxy group, a p-toluenesulfonyloxy group or a halogen atom; and M represents an alkali metal atom, provided that X does not represent a 2-chloro group and a 2,4-dichloro group.

That is, the objective compound represented by formula (I) can be produced by reacting an optically active glycol derivative having stereoconfiguration (S) represented by formula (II) of which stereoconfiguration is specified or an equivalent thereof with a dithiolate salt represented by formula (III). The compound represented by formula (II) can be used in an equimolar amount or an excess molar amount per the dithiolate salt represented by formula (III).

The equivalent of the optically active glycol derivative represented by formula (II) means a compound having reactivity similar thereto (that is, a compound which is not included in glycol derivatives, but provides the same product and has the similar reactivity). For example, the equivalent includes those wherein one of $X_1$ and $X_2$ represents a halogen atom such as Cl, Br and I, and the other represents a halogen atom, a methanesulfonyloxy group, a benzenesulfonyloxy group, or a p-toluenesulfonyloxy group. In other words, the compounds represented by formula (II) can be used as the starting material in the reaction according to the present invention.

A reaction temperature can be selected from the range of 0 to 100° C. Preferably, the reaction is carried out at around room temperature. The reaction time can be selected from the range of 0.5 to 24 hours.

The resulting compound is a mixture of geometrical isomers E and Z to the double bond in the compound, and the objective E-isomer represented by formula (I) can be readily isolated and purified by, e.g., silica gel column chromatography or fractional crystallization. Examples of solvent used for purification by fractional crystallization and recrystallization include ethanol, ethyl acetate, ether, hexane, acetone, and mixed solvents thereof.

Reaction 2

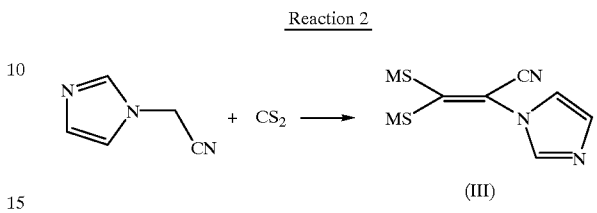

wherein M is the same as defined above.

The dithiolate salt represented by formula (III) can be produced by reacting 1-cyanomethylimidazole with carbon disulfide as shown in Reaction 2 in the presence of a base and an inert solvent. Any inert solvents can be used in the above reaction as long as they do not inhibit the progress of the reaction. Examples thereof include alcohols (e.g., methanol, ethanol, isopropanol), polar solvents (e.g., dimethyl sulfoxide (DMSO), dimethylformamide (DMF), acetonitrile), water, and mixed solvents thereof. Examples of the base include sodium carbonate, potassium carbonate, sodium hydroxide and potassium hydroxide. They can be used as they are in the form of solid or as a solution in an inert solvent. The amount (mol) of the base can be selected from the range of 2 to 8 times, preferably 4 to 6 times, the amount (mol) of 1-cyanomethylimidazole.

An optically active glycol derivative having stereoconfiguration (S) represented by formula (II) of which stereoconfiguration is specified can be produced according to Reactions 3 to 5 shown below.

Reaction 3

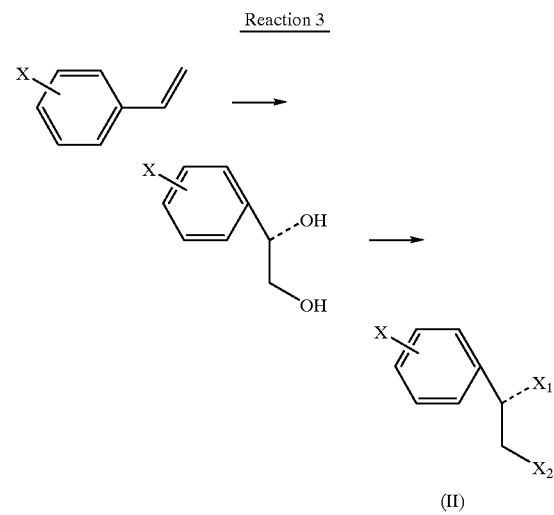

wherein X, $X_1$ and $X_2$ are the same as defined above.

That is, it can be produced by reacting an (S)-(substituted-phenyl)ethane-1,2-diol which can be produced stereoselectively from a substituted styrene according to the method described in *J. Org. Chem.*, 57:2768 (1992) with a suitable halogenating agent (e.g., thionyl chloride, phosphorus tribromide, carbon tetrachloride/triphenylphosphine), or an activating agent (i.e., methanesulfonyl chloride, toluenesulfonyl chloride, benzenesulfonyl chloride).

Reaction 4

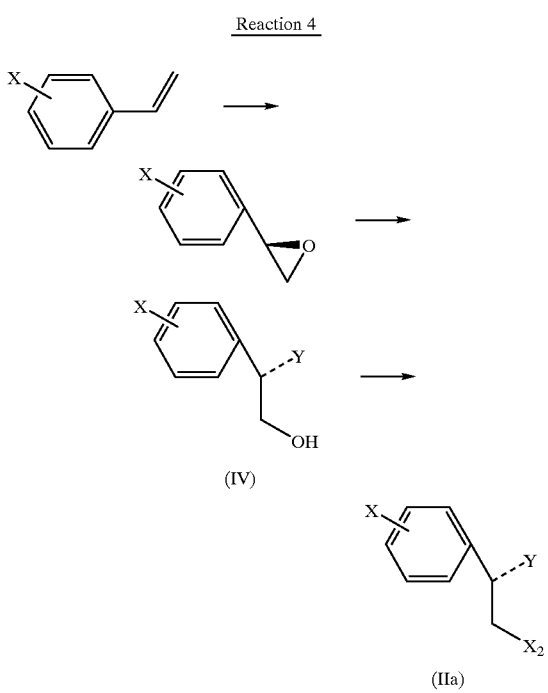

wherein Y represents a chlorine atom or a bromine atom; and X and $X_2$ are the same as defined above.

The compound represented by formula (IIa) can be produced by reacting an (R)-1-(substituted-phenyl) styrene oxide which can be produced stereoselectively from a substituted styrene according to the method described in *J. Am. Chem. Soc.,* 113:7063 (1991) with a halogenated hydrogen to prepare a haloalcohol represented by formula (IV) and then reacting the haloalcohol thus obtained with a suitable halogenating agent (e.g., thionyl chloride, phosphorus tribromide, carbon tetrachloride/triphenylphosphine) or an activating agent (e.g., methanesulfonyl chloride, toluenesulfonyl chloride, benzenesulfonyl chloride).

Reaction 5

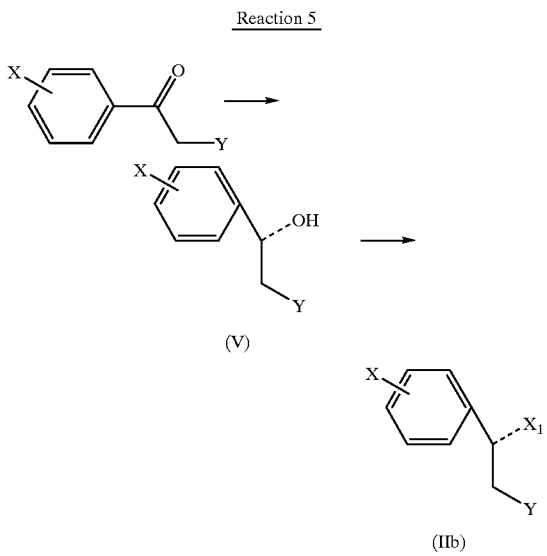

wherein Y represents a chlorine atom or a bromine atom; and X and $X_1$ are the same as defined above.

The compound represented by formula (IIb) can be produced by reacting a haloalcohol represented by formula (V) which can be produced stereoselectively from a substituted acetophenone derivative according to the method described in *Modern Synthetic Method,* 5:115 (1989) with a suitable halogenating agent (i.e., thionyl chloride, phosphorus tribromide, carbon tetrachloride/triphenylphosphine) or an activating agent (i.e., methanesulfonyl chloride, toluenesulfonyl chloride, benzenesulfonyl chloride).

The "salt" or "pharmaceutically acceptable salt" of the compound represented by formula (I) in the present invention includes a salt of the compound and an inorganic acid (e.g., hydrochloric acid, hydrobromic acid, sulfuric acid, nitric acid, phosphoric acid) or an organic acid (e.g., oxalic acid, succinic acid, tartaric acid, citric acid, valeric acid, methanesulfonic acid, p-toluenesulfnic acid).

The compound according to the present invention and pharmaceutically acceptable salts thereof are formed into pharmaceutically acceptable preparations suitable for oral administration or those suitable for painting treatment.

Examples of the preparation form include liquid formulation, tablet, emulsion, ointment, cream, lotion and poultice.

The amount to be administered varies depending upon age, body weight and administration form. In generalized treatment, the amount is normally at least 0.05 mg, preferably from 0.5 to 50 mg, per kg of body weight of adult and per day, and the preparation can be administered at one time or several times in parts in one day.

In a local treatment, the preparation is used as a painting preparation comprising an active ingredient of at least 0.001%, preferably 0.1 to 2%. The preparation is applied in an amount of 30 to 100 mg per $cm^2$.

The antifungal composition according to the present invention may be used in admixture with other antifungal agents or antibacterial agents (e.g., amphotericin B, trichomycin, varitotin, clotrimazole).

Optically active imidazole derivatives and salts thereof produced according to the present invention have a more excellent antifungal activity than the racemic mixture thereof. Thus, they are useful as preparations for preventing or treating mycoses of human and animals.

Preparation Examples, Formulation Examples and Test Example of the present invention will be shown below. However, the present invention is not limited thereto. Parts are all by weight unless otherwise indicated.

PREPARATION EXAMPLE 1

Synthesis of (R)-(E)-[4-(4-fluorophenyl)-1,3-dithicolan-2-ylidene]-1-imidazolylacetonitrile (Compound No. 1)

Potassium hydroxide (0.99 g) was added to DMSO (40 ml). A solution of 1-cyanomethylimidazole (1.05 g) and carbon disulfide (0.74 g) in DMSO (10 ml) was added thereto under cooling in a water bath. After stirring for 2 hours at room temperature, a solution of (S)-1-(4-fluorophenyl)ethane-1,2-bismethanesulfonate (1.9 g) in DMSO (10 ml) was added under cooling in a water bath, followed by stirring for 1.5 hour at room temperature. The resulting reaction mixture was poured into ice water and extracted with ethyl acetate. The ethyl acetate layer was washed with water and dried over anhydrous magnesium sulfate. The solvent was distilled off under reduced pressure, the residue was purified by silica gel column chromatography (ethyl acetate/n-hexane=⅓) to obtain a crystal, and the crystal was then recrystallized from a mixture of ethyl acetate and n-hexane. The yield was 0.59 g and the optical purity was 95.0%. The optical purity was calculated from area percentage in optically active HPLC (Chiralcel OD, Daicel Chemical Industry Ltd.).

PREPARATION EXAMPLE 2

Synthesis of (R)-(E)-[4-(2-chloro-4-bromophenyl) -1,3-dithiolan-2-ylidene]-1-imidazolylacetonitrile (Compound No. 2)

Potassium hydroxide (1.4 g) was added to DMSO (80 ml). A solution of 1-cyanomethylimidazole (1.5 g) and carbon disulfide (1.1 g) in DMSO (10 ml) was added thereto under cooling in a water bath. After stirring for 2 hours at room temperature, a solution of (S)-1-(2-chloro-4-bromo-phenyl) ethane-1,2-bismethanesulfonate (4.1 g) in DMSO (10 ml) was added under cooling in a water bath, followed by stirring for 2 hours at room temperature. The resulting reaction mixture was poured into ice water and extracted fifth ethyl acetate. The ethyl acetate layer was washed with water and dried over anhydrous magnesium sulfate. The solvent was distilled off under reduced pressure, the residue was purified by silica gel column chromatography (ethyl acetate/n-hexane=1/3) to obtain a crystal, and the crystal was then recrystallized from a mixture of ethyl acetate and n-hexane. The yield was 1.0 g and the optical purity was 95.5%.

Compounds of Examples are shown in Table 1 and the racemates thereof are shown in Table 2 as compounds of Comparative Examples.

TABLE 1

Compounds of Examples (I)

| Compound No. | Substituent X | Melting Point (° C.)/ Refractive Index (° C.) |
|---|---|---|
| 1 | 4-fluoro | m.p.: 75–76 |
| 2 | 3-chloro | nD: 1.3506 (26.3) |
| 3 | 4-bromo | m.p.: 136–137 |
| 4 | 4-chloro | m.p.: 93–94 |
| 5 | 2-fluoro | m.p.: 117–118 |
| 6 | 2-methyl | m.p.: 150–151 |
| 7 | 2,4-difluoro | m.p.: 89–90 |
| 8 | 2-bromo | m.p.: 154–155 |
| 9 | 2-difluoromethoxy | nD: 1.6071 (26.8) |
| 10 | 2-trifluoromethyl | nD: 1.5658 (24.5) |
| 11 | 2,4-dibromo | m.p.: 187 |
| 12 | 2-chloro-4-fluoro | m.p.: 155–156 |
| 13 | 2-chloro-4-bromo | m.p.: 156–157 |

TABLE 2

Compounds of Comparative Examples
(racemates of compounds No. 1 to 13)

| Compound No. | Substituent X | Melting Point (° C.)/ Refractive Index (° C.) |
|---|---|---|
| 1' | 4-fluoro | m.p.: 97–98 |
| 2' | 3-chloro | nD: 1.5117 (26.3) |
| 3' | 4-bromo | m.p.: 99–100 |
| 4' | 4-chloro | m.p.: 119–120 |
| 5' | 2-fluoro | m.p.: 117–118 |
| 6' | 2-methyl | m.p.: 120–121 |
| 7' | 2,4-difluoro | m.p.: 86–87 |
| 8' | 2-bromo | nD: 1.3696 (25.3) |
| 9' | 2-difluoromethoxy | nD: 1.5942 (26.4) |
| 10' | 2-trifluoromethyl | nD: 1.5906 (24.9) |
| 11' | 2,4-dibromo | m.p.: 165–166 |
| 12' | 2-chloro-4-fluoro | m.p.: 154–155 |
| 13' | 2-chloro-4-bromo | m.p.: 129–131 |

Formulation Examples of preparations will be shown below. However, the present invention is not limited thereto.

FORMULATION EXAMPLE 1

| Compound of the invention | 10 parts |
|---|---|
| Magnesium stearate | 10 parts |
| Lactose | 80 parts |

The above ingredients were uniformly mixed and the mixture was made into powders or fine particles to obtain a powder preparation.

FORMULATION EXAMPLE 2

| Compound of the invention | 20 parts |
|---|---|
| Starch | 10 parts |
| Lactose | 15 parts |
| Ethylcellulose | 20 parts |
| Polyvinyl alcohol | 5 parts |
| Water | 30 parts |

The above ingredients were uniformly mixed and kneaded, the mixture was ground and made into particles, and the particles were sifted to obtain a granular preparation.

FORMULATION EXAMPLE 3

| Compound of the invention | 0.5 part |
|---|---|
| Nonionic surfactant | 2.5 parts |
| Physiological saline solution | 97 parts |

The above ingredients were mixed under heating, and then sterilized to obtain an injection.

FORMULATION EXAMPLE 4

| Compound of the invention | 0.01 part |
|---|---|
| 0.5% Carboxymethylcelluolse | 99.99 parts |

The above ingredients were suspended to obtain a suspension.

FORMULATION EXAMPLE 5

| Compound of the invention | 1 part |
|---|---|
| Polyethylene glycol 400 | 99 parts |

The above ingredients were mixed and dissolved to obtain a liquid preparation for painting.

PREPARATION EXAMPLE 6

| Compound of the invention | 2 parts |
|---|---|
| Polyethylene glycol 400 | 49 parts |
| Polyethylene glycol 4000 | 49 parts |

The above ingredients were mixed and dissolved under heating and then cooled to obtain an ointment.

FORMULATION EXAMPLE 7

| Compound of the invention | 3 parts |
|---|---|
| 1.2-Propanediol | 5 parts |
| Glycerol stearate | 5 parts |
| Spermaceti | 5 parts |
| Isopropyl myristate | 10 parts |
| Polysorbate | 4 parts |

The above ingredients were mixed under heating, and then cooled. While stirring, 68 parts of water is addled thereto to obtain a cream.

FORMULATION EXAMPLE 8

One part of the compound of the invention, 5 parts of benzyl alcohol, 30 parts of ethanol and 47 parts of propylene glycol were mixed and dissolved. Then, an aqueous solution composed of 1 part of Hiviskwako 104 and 15 parts of purified water was added thereto to obtain a uniform solution. Next, 1 part of diisopropanolamine was added thereto with stirring to obtain a gel preparation.

PREPARATION EXAMPLE 9

One part of the compound of the invention was dissolved into 5 parts of benzyl alcohol and 5 parts of diethyl sebacate. Then, 5 parts of ethyl alcohol, 6 pairs of stearyl alcohol, 1 part of sorbitan monostearate and 8 parts of polyoxyethylene monostearate were added thereto, and dissolved under heating at 70° C. While keeping at 70° C., 69 parts of purified water which had been heated to 70° C. were added to the resulting uniform solution, and then cooled with stirring to obtain a cream composition.

TEST EXAMPLE

In vitro antifungal activity of compounds against dormatophytes

Sample strains:

*Trichophyton mentagrophytes* IFO 5811
*Trichophyton mentagrophytes* TIMM 2789
*Trichophyton rubrunm* IFO 6204
*Trichophyton rubrum* IFO 5808

Preparation of inoculation fungal solution:

To a strain cultured on Sabouraud's glucose agar (SGA) slant medium at 27° C. for 1 to 2 weeks was added 0.1% (v/v) Tween 80-added sterilized physiological saline solution, followed by rubbing with a platinum spatula. The resulting suspension of conidia was filtered through a sterilized gauze to eliminate mycelium mass. Thereafter, the conidia was counted by an erythrocytometer (Thoma) The suspension of the conidia was diluted with 0.1% (v/v) Tween 80-added sterilized physiological saline solution so as to have a concentration of $1 \times 10^6$ conidia/ml to obtain an inoculation fungal solution.

Preparation of drug:

Each compound was dissolved into dimethyl sulfoxide (DMSO) to prepare a diluent having a half concentration. The concentration of DMSO in a medium was adjusted to hair 1% (v/v).

Measurement of antifungal activity:

A SGA plate medium containing a given amount of a compound (20 ml/dish) was prepared. A loopful of the inoculation fungal solution was applied in the form of a line to each plate medium at a length of about 15 mm, and was allowed to stand for cultivation at 27° C. for 7 days. The minimum inhibitory concentration (MIC) of the compound at which a growth of a microorganism cannot be visually recognized was determined. The results are shown in Table 3.

TABLE 3

MIC value against Trichophyton ($\mu$g/ml)

| | | T. mentagrophytes | | T. rubrum | |
|---|---|---|---|---|---|
| Compound No. | | IFO 5811 | TIMM 2789 | IFO 6204 | IFO 5805 |
| 1 | (R) | 0.64 | 0.32 | 0.16 | 0.32 |
| 1' | Rasemic | >0.64 | 0.64 | 0.32 | 0.64 |
| 2 | (R) | 0.64 | 0.32 | 0.16 | 0.64 |
| 2' | Rasemic | >0.64 | >0.64 | 0.64 | >0.64 |
| 3 | (R) | >0.08 | >0.08 | 0.08 | >0.08 |
| 3' | Rasemic | >0.08 | >0.08 | >0.08 | >0.08 |
| 4 | (R) | >0.08 | >0.08 | 0.08 | >0.08 |
| 4' | Rasemic | >0.08 | >0.08 | >0.08 | >0.08 |
| 5 | (R) | 0.08 | 0.02 | 0.01 | 0.04 |
| 5' | Rasemic | 0.16 | 0.04 | 0.01 | 0.04 |
| 6 | (R) | 0.32 | 0.08 | 0.08 | 0.16 |
| 6' | Rasemic | 0.32 | 0.32 | 0.08 | 0.32 |
| 7 | (R) | 0.16 | 0.04 | 0.02 | 0.08 |
| 7' | Rasemic | 0.32 | 0.08 | 0.04 | 0.16 |
| 8 | (R) | 0.04 | 0.02 | 0.01 | 0.01 |
| 8' | Rasemic | 0.16 | 0.04 | 0.02 | 0.04 |
| 9 | (R) | 1.28 | 0.64 | 0.32 | 0.32 |
| 9' | Rasemic | 2.56 | 1.28 | 0.64 | 0.64 |
| 10 | (R) | 0.32 | 0.16 | 0.04 | 0.04 |
| 10' | Rasemic | 0.64 | 0.32 | 0.08 | 0.08 |
| 11 | (R) | 0.04 | 0.02 | 0.01 | 0.02 |
| 11' | Rasemic | 0.04 | 0.02 | 0.02 | 0.04 |
| 12 | (R) | 0.04 | 0.02 | 0.02 | 0.02 |
| 12' | Rasemic | 0.16 | 0.04 | 0.04 | 0.04 |
| 13 | (R) | 0.02 | 0.01 | 0.01 | 0.01 |
| 13' | Rasemic | 0.04 | 0.02 | 0.02 | 0.02 |

While the invention has been described in detail and with reference to specific embodiments thereof, it will be apparent to one skilled in the art that various changes and modifications can be made therein without departing from the spirit and scope thereof.

This application is based on Japanese application Hei 8-346692, the entire content of which is incorporated hereinto by reference.

What is claimed is:

1. An optically active (R)-(E)-(4-substituted-phenyl-1,3-dithiolan-2-ylidene)-1-imidazolylacetonitrile derivative represented by the following formula (I) or a sat thereof:

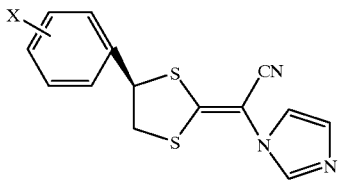

(I)

wherein X represents 2 halogen atoms which are the same or different from each other, provided that X does not represent a 2,4-dichloro group.

2. The optically active (R)-(E)-(4-substituted-phenyl-1,3-dithiolan-2-ylidene)-1-imidazolylacetonitrile derivative or the salt thereof according to claim 1, wherein X is selected from the group consisting of a 2,4-difluoro group, a 2,4-dibromo group, a 2-chloro-4-fluoro group, and a 2-chloro-4-bromo group.

3. An antifungal composition comprising as an active ingredient the optically active (R)-(E)-(4-substituted-phenyl-1,3-dithiolan-2-ylidene)-1-imidazolylacetonitrile derivative according to claim 1 or a pharmaceutically acceptable salt thereof, optionally together with a pharmaceutically acceptable carrier or diluent.

4. A method for preventing or treating local or generalized mycoses comprising administrating to human or animals in need of such prevention or treatment a pharmaceutically effective amount of the optically active (R)-(E)-(4-substituted-phenyl-1,3-dithiolan-2-ylidene)-1-imidazolylacetonitrile derivative according to claim 1 or a pharmaceutically acceptable salt thereof, together with a pharmaceutical acceptable carrier or a diluent.

5. The method according to claim 4, which prevents or treats local mycotic infection, mucosa infection or generalized mycotic infection caused by the genus Trichophyton, Candida or Aspergillus.

* * * * *